United States Patent [19]

Sachdeva et al.

[11] Patent Number: 5,607,435
[45] Date of Patent: Mar. 4, 1997

[54] INSTRUMENT FOR ENDOSCOPIC-TYPE PROCEDURES

[75] Inventors: Rohit C. L. Sachdeva, Plano, Tex.; Petrus A. Besselink, AT Enschede, Netherlands

[73] Assignee: Memory Medical Systems, Inc., Plano, Tex.

[21] Appl. No.: 247,779

[22] Filed: May 23, 1994

[51] Int. Cl.⁶ ................................................... A61B 17/00
[52] U.S. Cl. ........................... 606/139; 606/13; 606/80; 606/139; 606/167; 606/205; 359/819; 359/820; 600/129; 600/143; 600/151; 600/172
[58] Field of Search ....................... 606/13–17, 139, 606/144, 148, 145, 151, 205, 207, 80, 167, 170; 604/281; 600/108, 114, 129, 143, 150, 151, 172, 176; 359/819–820

[56] References Cited

U.S. PATENT DOCUMENTS

| 3,890,977 | 6/1975 | Wilson . | |
|---|---|---|---|
| 4,665,906 | 5/1987 | Jervis . | |
| 4,966,439 | 10/1990 | Althaus et al. | 359/820 |
| 5,052,300 | 10/1991 | Josse | 102/201 |
| 5,109,830 | 5/1992 | Cho | 600/150 |
| 5,230,621 | 7/1993 | Jacoby | 600/108 |
| 5,242,448 | 9/1993 | Pettine et al. . | |
| 5,254,130 | 10/1993 | Poncet et al. | 606/206 |
| 5,281,214 | 1/1994 | Wilkins et al. | 606/15 |
| 5,281,236 | 1/1994 | Bagnato et al. | 606/139 |

FOREIGN PATENT DOCUMENTS

| 0481685 | 4/1992 | European Pat. Off. . | |
|---|---|---|---|
| 0529675 | 8/1992 | European Pat. Off. . | |
| 0566280 | 10/1993 | European Pat. Off. . | |
| 4136861 | 5/1993 | Germany . | |
| 680041 | 6/1992 | Switzerland | 600/114 |
| 9214506 | 9/1992 | WIPO . | |

Primary Examiner—Michael Powell Buiz
Assistant Examiner—Jeffrey A. Schmidt
Attorney, Agent, or Firm—Wood, Herron & Evans P.L.L.

[57] ABSTRACT

The present invention is an instrument (10) which includes a tubular section (12) having a wall (13) made of a material exhibiting superelastic characteristics and a delivery tube (14) having a bore (15) through which the tubular section (12) passes. The instrument (10) may be adapted for use in medical/dental and non-medical procedures. The superelastic character of the wall material is used in combination with the delivery tube (14) to alternately restrict the shape of the wall (13) and allow it to change to its unconstrained shape. Thus, the wall (13) can be sufficiently deformed to permit the tubular section (12) to pass in and out of and through the delivery tube (14) while at the same time enabling the tubular section (12) to have a shape when extended outside of the delivery tube (14) that is sufficiently bent or curved to be suitable for performing a desired function, for example a medical or dental procedure inside a patient's body. In this way, the delivery tube (14) enables the tubular section (12) to reach the site of the procedure through more narrow insertion paths, and in the case of medical/dental applications, with less trauma to the surrounding tissue along the insertion path. Because it can be inserted through more narrow pathways, the tubular section (12) can be delivered to more remote and harder to reach locations.

30 Claims, 5 Drawing Sheets

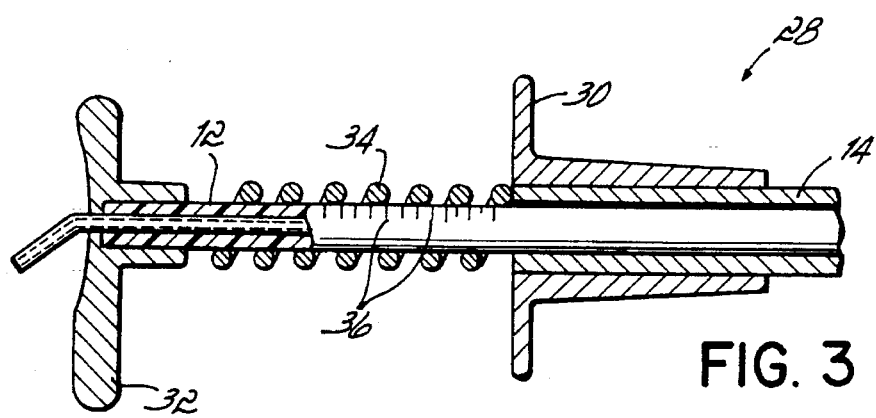
FIG. 3
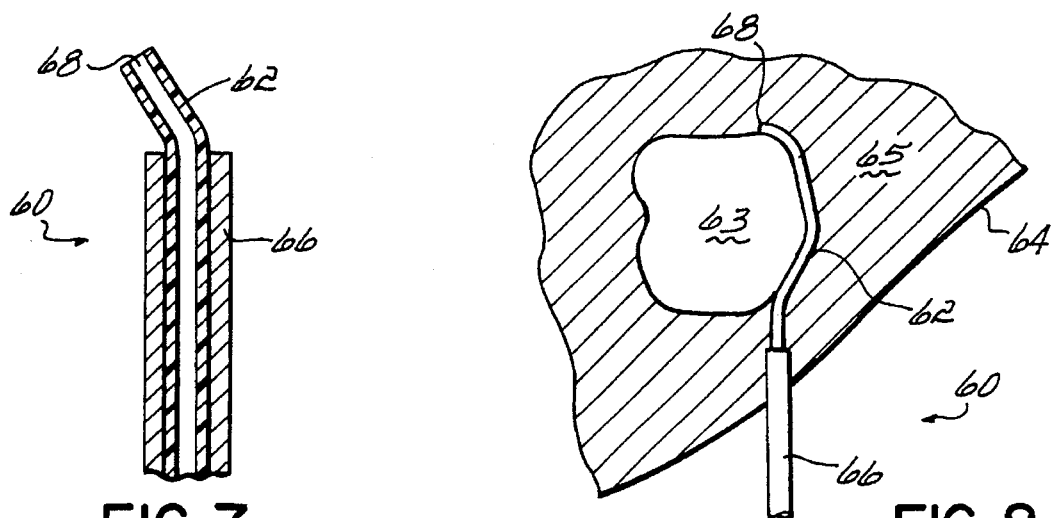
FIG. 7
FIG. 8
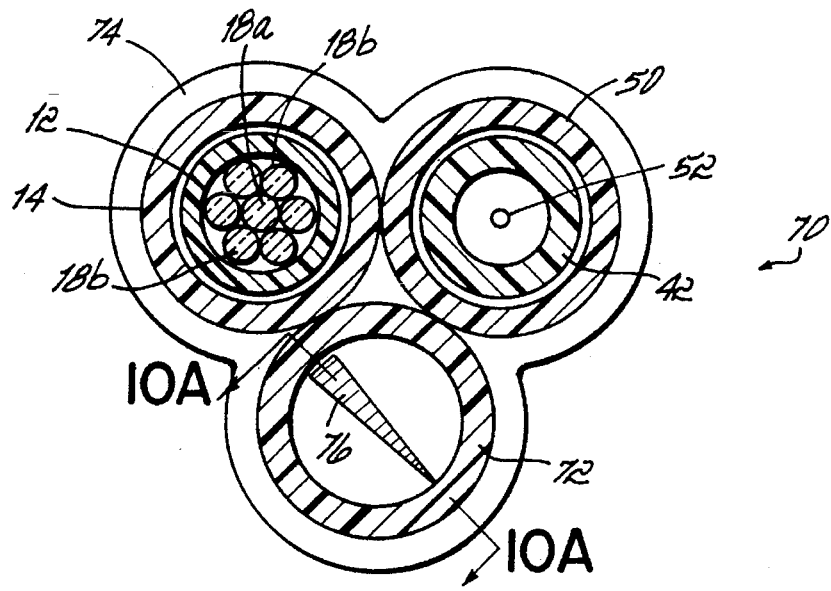
FIG. 9

INSTRUMENT FOR ENDOSCOPIC-TYPE PROCEDURES

FIELD OF THE INVENTION

The present invention is related to instruments useful in endoscopic-type procedures, and more particularly, to medical/dental instruments useful in endoscopic diagnostic and surgical procedures, such as arthroscopic, endotracheal and laproscopic procedures.

BACKGROUND OF THE INVENTION

Surgical and other medical operations are often performed at sites deep within a patient's body. In the past, the only way to perform such medical procedures was to cut a large enough incision in the patient's body to expose the operating site sufficiently to permit direct access by a physician. However, such operations typically caused a great deal of trauma to the affected tissue requiring lengthy periods for recovery and causing the patient substantial pain and suffering. With technological advances in the medical profession, more and more of these medical operations are being performed using less invasive endoscopic (e.g., arthroscopic and laproscopic procedures) and similar procedures. In general, endoscopic procedures include using an instrument having a delivery tube with an inner bore through which a tool can be inserted. Depending on the medical procedure, the delivery tube can have a variety of shapes (e.g., straight, curved, etc. . . . ) and be either rigid or flexible. With such an instrument, the delivery tube is usually inserted into the patient's body by way of either a comparatively small incision or a body orifice and through a body cavity or hollow organ to the site desired. In this way, any trauma to the patient's body can be generally limited to surrounding tissue along the insertion path of the delivery tube. One such endoscopic instrument incorporates a fiber optic system. Image transmission by optical fibers is widely used in medical instruments for viewing inside the human body and in a variety of other applications. Such instruments have been used for diagnostic purposes and to observe during operating procedures. Optical fibers have also been developed to carry high-power laser beams for cauterizing, cutting and drilling. With such instruments, a lens affixed to an optical fiber is inserted through the rigid delivery tube to the desired site inside the patient's body. However, once delivered to the site, the lens is typically difficult to maneuver and manipulate in order to view the site in its entirety, or adequately laser cauterize, cut or drill at the site. This is especially true when the operating site is deep in the patient's body, far from the point of entry of the instrument into the body or at the end of a curved or otherwise tortuous path through the body.

Because of the difficulties encountered in maneuvering and manipulating such fiber optic instruments, some medical procedures must still be preformed without the aid of such instruments. For example, a number of periodontal procedures are preformed with the surgeon having to rely solely on his/her sense of touch. Periodontology includes the treatments of patients having diseased gums which have separated from around the root of a patient's tooth. It is sometimes necessary to remove diseased tissue from the inside surface of the patient's gum around the affected tooth and to remove calculus from the tooth root surface. Having to rely solely on the sense of touch did not always ensure that the procedure would be preformed thoroughly (i.e., that all the diseased tissue or calculus would be removed). If the physician needed to observe around the tooth root during either procedure, an incision would typically have to be made through the gum tissue in order to open up the area for viewing. As another example, the existing root of a patient's tooth is often used as an anchor for a prosthetic tooth or crown. In such a procedure, the root canal should be thoroughly sterilized and filled with a suitable filler to prevent the subsequent intrusion of bacteria and decay of the root. However, with prior instruments, it is not always possible to ensure that the root canal has been completely sterilized and filled.

Even when a conventional fiber optic instrument can be used to observe an operating procedure (e.g., an arthroscopic ligament repair), it is often necessary to tilt the delivery tube at various angles in order to properly observe the entire procedure. Such manipulation of the delivery tube typically causes stretching of and additional trauma to the surrounding tissue, resulting in longer recovery periods and in some cases additional discomfort and pain for the patient. In addition, during such procedures other endoscopic delivery tubes are typically inserted through separate incisions in the patient's body to gain simultaneous access to the operating site. This permits multiple tools to be used at one time. The more incisions made, however, the more trauma to the surrounding tissue, the more pain and suffering likely to be endured by the patient and again the longer the recovery period. For some operating sites, such as at the end of or along a narrow cavity or hollow organ, space constraints only allow one delivery tube to be used at a time. In such a situation, some operations cannot be simultaneously observed while they are being performed. Therefore, there is also a need for a multiple function instrument which permits more than one tool to be used at the same time through a single incision, cavity or hollow organ.

Similar endoscopic-type instruments have also been used to perform visual inspections deep within objects, such as a bore or other cavity in a mechanical component or machine. However, the ability of such instruments to inspect a site at various angles is typically limited due to the lack of maneuverability of such instruments. Such limitations can require the object to be dismantled in order to perform an adequate inspection, thereby increasing the cost of inspection. In addition, if it cannot be dismantled, the object may have to remain uninspected, thereby increasing the risk of an undetected defect.

During some endoscopic procedures, it may become necessary to suture tissue. Currently, endoscopic-type suturing instruments have been developed to suture tissue located in a patient's body without having to make a major incision to gain direct access to the suture site. For example, long and narrow forceps have been developed for gripping a conventional curved surgical needle and enabling tissue to be sutured deep in a patient's body. Such a suturing instrument is less invasive than cutting a large enough incision to permit direct access by the physician. However, the uses for such suturing instruments are still limited due to the size of the instrument, in particular its diameter, and the shape of the needle being held. A number of areas in the patient's body cannot be reached except through pathways (i.e., cavities, hollow organs, etc. . . . ) that are far to narrow to receive conventional forceps type suturing instruments. In addition, another incision or entry site into the body is often necessary in order to view the procedure. Thus, there is a need for an even less invasive suturing instrument, and one that permits the suturing of tissue in even harder to reach locations in the patient's body than heretofore possible with such a prior conventional endoscopic-type suturing instrument.

Another endoscopic instrument employs a solid superelastic wire which is made to curve when it exists the delivery tube in order to encircle and thereby aid in locating cancerous tumors. One such wire locator instrument, commonly referred to by the trademark Homer Mammalock, is used to help locate cancerous tumors in a woman's breast. Because such tumors are typically denser than the surrounding fatty tissue, the locator wire tends to encircle rather than pass through the tumor. Being surrounded by the locator wire, the tumor is easier to locate using external imaging systems, like conventional x-rays. Even though such wire locator instruments have had some success, there is still a need to improve the ability of such instruments to locate tumors.

SUMMARY OF THE INVENTION

An objective of the present invention is to provide an endoscopic-type fiber optic system which can be readily manipulated to point at various angles.

A related objective of the preceding invention is to provide such an instrument capable of reaching various sites in a patient's body, including sites accessible through a small diameter cavity such as a tooth root canal or a hollow organ such as a blood vessel or sites at the end of a curving or otherwise tortuous path such as around a tooth root.

An additional related objective of the preceding invention is to provide such an instrument for visually inspecting various sites in a patient's body.

Another related objective of the preceding invention is to provide such an instrument for performing various procedures at sites in a patients body using a high-power laser beam.

Another objective of the present invention is to provide a medical instrument suitable for suturing at locations inside a patient's body with limited trauma being caused to tissue located along the path of insertion.

A related objective of the preceding invention is to provide such a medical instrument suitable for suturing at hard to reach locations inside the patient's body, including locations accessible through a small diameter cavity or hollow organ.

A further objective of the present invention is to provide a medical instrument for better locating cancerous tumors or similar masses in a patient's body using an external imaging system.

An additional objective of the present invention is to provide a medical instrument which allows simultaneous use of a fiber optic system and one or more other tools each of which can be readily manipulated and maneuvered at a site in a patient's body during an endoscopic procedure, such as arthroscopic, endotracheal and laproscopic procedures.

Broadly, the present invention is an instrument which includes a tubular section having a wall made of a material exhibiting superelastic characteristics, and a delivery tube having a bore through which the tubular section passes. The instrument is adaptable for use in medical and non-medical procedures. The superelastic character of the wall material is used in combination with the delivery tube to alternately restrict the shape of the wall and allow the wall to change to its unconstrained condition. Thus the wall can be sufficiently deformed to permit the tubular section to pass in and out of and through the delivery tube while at the same time enabling the tubular section to have a shape when extended outside of the delivery tube that is sufficiently bent or curved to be suitable for performing a desired function, for example a medical procedure inside a patient's body. In this way, the delivery tube enables the tubular section to reach the site of the procedure through more narrow insertion paths, and in the case of medical applications, with less trauma to the surrounding tissue along the insertion path. Thus the present invention is particularly useful in medical diagnostic and surgical procedures performed inside of or through a hollow cavity or organ of a patient's body. Because it can be inserted through more narrow pathways, the tubular section can be delivered through narrower cavities and hollow organs to more remote and harder to reach locations in the body in a less invasive manner. Because of its superelastic characteristics, the tubular section can also be made to follow curved or more tortuous pathways without developing a permanent set.

An instrument according to the principles of the present invention can be adapted to view the inside of a patient's body for diagnostic purposes or during an operation or inside of inanimate objects. One embodiment of such a viewing instrument includes a tubular section with a leading end mounting a fiber optic lens connected to an optical fiber element running through the length of the tubular section. When unconstrained, the leading end of the tubular section has a desired bend or curve relative to the balance of the tubular section. When the tubular section is disposed in the delivery tube, its shape is constrained to conform to that of the delivery tube. Thus, the leading end bends at an angle as it extends out of the delivery tube. The tubular section can be made so that the angle at which its leading end bends changes as it extends further out of or retracted back into the delivery tube. In addition, with its wall being made of a sufficiently stiff superelastic material, the tubular section and thus its leading end can be axially rotated to view the surrounding area in a 360° arc. In this way, a particular site of interest in the patient's body can be thoroughly observed, even if its location is at the end of a narrow cavity or hollow organ deep in the patient's body or far from where the instrument first enters the body. Such maneuverability has similar advantages for a fiber optic instrument adapted for cauterizing, cutting and drilling with high-power laser beams.

In another embodiment of a medical instrument according to the principles of the present invention, the tubular section is formed into the shape of a surgical needle for suturing inside a patient's body. The leading end of the tubular section can have the conventional C-shape of a surgical needle or any other bent or curved shape that facilitates suturing, with its tip being in the form of a sharp point. Because of its superelastic characteristics, this surgical needle can remain straight as it is inserted through the delivery tube without developing a permanent set (i.e., without substantial permanent deformation). While in the delivery tube and in this substantially straight condition, the needle can be delivered to the suturing site through narrower paths then heretofore possible, without substantial trauma being caused along the path of insertion. Once at the suture site, the surgical needle (i.e., tubular section) is extended out of the leading end of the delivery tube, returning it to its original curved or bent shape for suturing. Because the shape of the tubular needle section is variable, suturing can be performed at a variety of angles and orientations relative to the delivery tube. The suture thread or wire is operatively disposed in the bore of the tubular section so as to remain in position to form a suture upon removal of the tubular needle.

In another embodiment of the present invention, the tubular section can be adapted to curl around a cancerous tumor or similar mass upon exiting the delivery tube in a manner similar to that of prior locator wires. However, in order to improve the likelihood of locating the tumor or similar mass, the bore of the tubular section is used to inject a radiopaque or other suitable type of dye into the area around the tumor mass to facilitate locating it using an external imaging system, such as an X-Ray machine.

Multiple instruments according to the present invention can be combined by securing two or more delivery tubes in a juxtaposed lengthwise relationship. By being joined together in this manner, the multiple delivery tubes can be inserted through a single incision, cavity, hollow organ, or other pathway through a patient's body or an object rather than through two or more such pathways.

The above and other objectives, features, and advantages of the present invention will become apparent upon consideration of the detailed description and the appended drawings.

BRIEF DESCRIPTION OF THE DRAWINGS

FIG. 3 is a sectional side view of an actuating mechanism at the proximal end of the delivery tube of FIG. 1;

FIG. 7 is a sectional side view of a medical instrument for locating tumors and similar masses in a patient's body according to the present invention, with its tubular section partially extended from the distal end of the delivery tube;

FIG. 8 is a sectional side view of the tubular locator of FIG. 7 in position to inject a dye around a tumor;

FIG. 9 is a sectional end view of a multiple component medical instrument for preforming a variety of functions according to the present invention, with a plurality of delivery tubes joined together in a juxtaposed lengthwise relationship;

DETAILED DESCRIPTION OF THE INVENTION

Although the present invention is herein described in terms of specific embodiments, it will be readily apparent to those skilled in this art that various modifications, rearrangements, and substitutions can be made without departing from the spirit of the invention. The scope of the present invention is thus only limited by the claims appended hereto. In the following description, the same designation numbers have been used for similar structural elements wherever appropriate to simplify the description.

Figure 1:
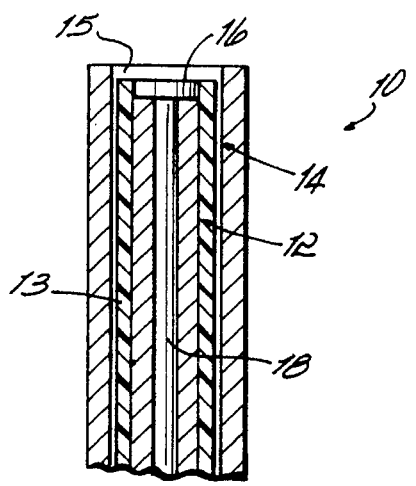
FIG. 1 is a sectional side view of an instrument incorporating fiber optics according to the present invention, with its fiber optic tubular section fully retracted in the delivery tube.
Figure 2:
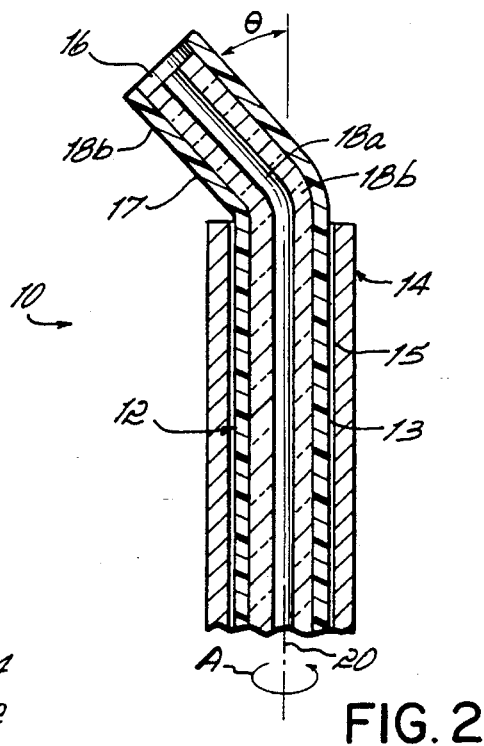
FIG. 2 is a sectional side view of the instrument of FIG. 1, with its tubular section partially extended from the distal end of the delivery tube.

Referring to FIGS. 1–3, a medical instrument 10 incorporating fiber optics according to the present invention, includes a tubular section having a wall 13 made of a material exhibiting superelastic characteristics and a delivery tube 14 having a bore 15 through which the tubular section 12 passes. The tubular section 12 has a leading end 17 mounting a fiber optic lens 16 operatively connected to a bundle of optical fibers 18 running through the length of the tubular section 12. Bundle 18 includes a central image transmitting fiber 18a surrounded by a plurality of illuminating optical fibers 18b. The structure of fiber optic lenses and fiber bundles are well known in the art and therefore are not included herein in detail. For example, see U.S. Pat. Nos. 5,073,048 and 5,190,028, each being incorporated herein by reference in its entirety. When extended from the distal end of delivery tube 14 (i.e., unconstrained), the leading end 17 of the tubular section 12 is bent or curved relative to a longitudinal axis 20 of the balance of the tubular section 12 remaining in the delivery tube 14. When the leading end 17 of the tubular section 12 is fully retracted in the delivery tube 14, its shape is constrained to conform to that of the delivery tube 14. The delivery tube 14 is sufficiently rigid to maintain the tubular section 12 in its constrained shape. The leading end 17 bends at an angle θ as it extends out of the delivery tube 14. The tubular section 12 can be formed according to well known techniques for shaping superelastic structures so that the angle θ at which its leading end 17 bends changes as it extends further out of or is retracted back into the delivery tube 14. In addition, with its wall 13 being made of a sufficiently stiff superelastic material, the tubular section 12 and in turn its leading end 17 can be axially rotated around axis 20 (see arrow A) to view the surrounding area in a 360° arc, thus providing the fiber optics with even more maneuverability. In this way, a particular site of interest in a patient's body can be thoroughly observed, even if its location is at the end of a narrow cavity, at the end of a hollow organ deep in the patient's body or far from where the instrument 10 first enters the body. Such maneuverability has similar advantages for the fiber optic instrument 10 adapted for cauterizing, burning, cutting or drilling with high-power laser beams. The imaging fiber optic system 16 and 18 used in instrument 10 could be replaced with a fiber optic system (not shown) suitable for producing high-power laser beams, like that disclosed in U.S. Pat. Nos. 5,163,935 and 5,242,437, each being incorporated herein by reference in its entirety. This degree of maneuverability is also possible with any instrument incorporating the principals of the present invention.

Figure 2A:
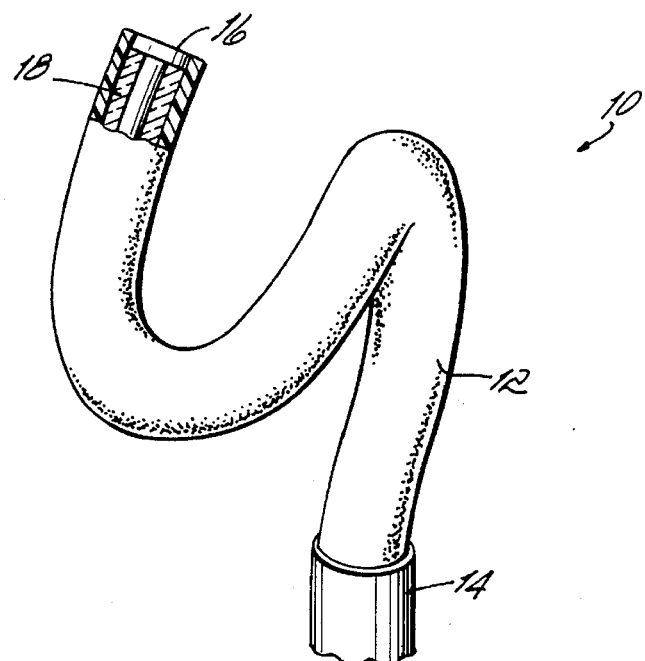
FIG. 2A is a partially broken away perspective view of a modified version of the instrument of FIG. 1, with its tubular section being shaped like a coil when extended from the distal end of the delivery tube.

Referring to FIG. 2A, because of its superelastic characteristics, the tubular section 12 can also be made to curl or coil around tortuous paths, such as around a tooth root (not shown) without developing a permanent set when retracted back into the delivery tube 14. In addition, because of the flat elastic response exhibited by superelastic materials, the force needed to straighten out even a coiled tubular section 12 and move the tubular section 12 through the delivery tube 14 can be relatively low. When used to perform a procedure down a rigid cavity or hollow organ, such as to view and/or sterilize (burn) the root canal of a tooth, the superelastic characteristics of the tubular section 12 would enable it to have the stiffness to be forced down into the root canal and yet still conform to the shape of the canal, even when the original shape of the tubular section 12 is different than that of the root canal.

Figure 2B:
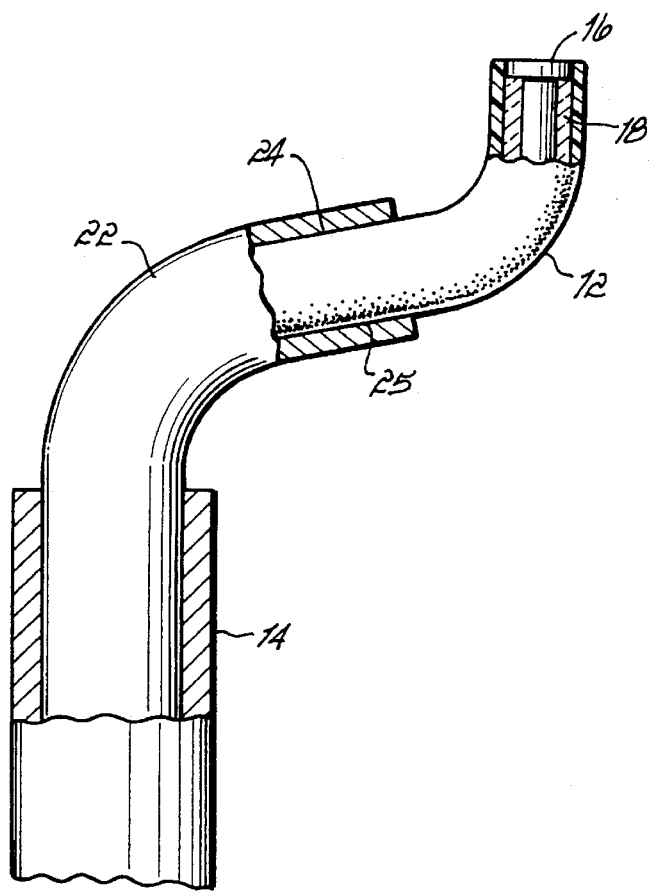
FIG. 2B is a partially broken away sectional view of a modified version of the instrument of FIG. 1, with its fiber optic tubular section being concentrically disposed within an intermediate tubular section, with both tubular sections shown extended from the distal end of the delivery tube in a telescopic manner.

Referring to FIG. 2B, the instrument 10 could further be modified to include another tubular section 22 having a bore 24 formed by a wall 25 made of a material exhibiting superelastic characteristics. The tubular section 12 would then be concentrically disposed within the intermediate tubular section 22 which is likewise disposed within the delivery tube 14. The intermediate tubular section 22 is similar to the tubular section 12 in that when extended from the delivery tube 14 (i.e., unconstrained), the leading end of tubular section 22 bends or curves relative to the balance of the tubular section 22 remaining in the delivery tube 14. Likewise, when the leading end of tubular section 22 is fully retracted in the delivery tube 14, its shape is constrained to conform to that of the delivery tube 14. When the tubular section 22 extends out of the distal end of delivery tube 14, the wall 25 of tubular section 22 is made out of a sufficiently rigid superelastic material to function as a delivery tube for tubular section 12. This may be accomplished by making tubular section 22 out of a more rigid or stronger superelastic material than that used to make tubular section 12. As can be seen from FIG. 2B, the first tubular section 12 can be made to curl in one direction and the intermediate tubular section 22 can be made to curl in the opposite direction, thereby increasing the maneuverability of the instrument 10. Thus, one or more tubular sections like tubular section 22 can be used to maneuver the fiber optic system or any other tool through a curving or otherwise tortuous path into position to perform the procedure desired.

Figure 10A:
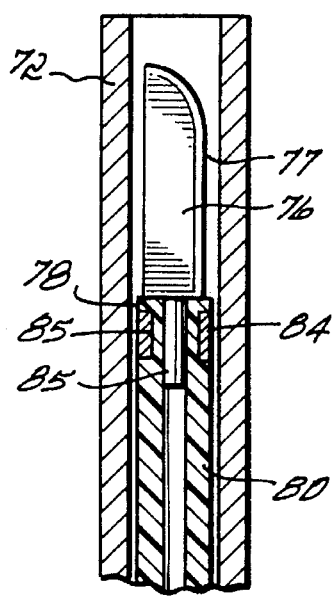
FIG. 10A is an enlarged sectional side view of the knife blade and delivery tube component of the instrument of FIG. 9 taken along lines 10A—10A, with its tubular section fully retracted within the delivery tube.

It is envisioned that any tubular section according to the principles of the present invention may be in the form of a capillary tube running the full length and extending out the proximal end of the delivery tube or the tubular section may be a separate element mounted to the distal end of a capillary tube made of a material other than a superelastic material. It is also envisioned that the fiber optic tubular section 12 could be replaced with any other tool adapted to slide in and out and through tubular section 22. One or more tubular sections 22 could then be used to provide additional manueverability for the tool. For example, a drill bit 79 mounted on the end of a bendable straight shaft could be substituted for the fiber optic tubular section 12. The drill bit could be mounted in a conventional manner to any suitably flexible shaft, including a shaft made of a superelastic material. The bit could also be mounted to a shaft in the same manner, described hereafter, that tool 76 is mounted to tubular section 80 (see FIGS. 10A and 10C).

Referring to FIG. 3, any suitable actuating mechanism 28 may be used to move the tubular section 12, or any other tubular section according to the present invention, in and out of and through its delivery tube 14. For example, the actuating mechanism 28 may include a finger grip 30 fixed to the proximal end of delivery tube 14 and a thumb handle 32 fixed to the rear end of tubular section 12. A compression coil spring 34 is disposed between the finger grip 30 and thumb handle 32 and around the tubular section 12. Spring 34 provides a positive bias for forcing the leading end 17 of tubular section 12 to retract back into the leading end of delivery tube 14. The outer surface of tubular section 12 located between grip 30 and handle 32 is graduated with a plurality of spaced lines 36 for measuring the relative longitudinal displacement between tubular section 12 and delivery tube 14. The ability to measure this axial relationship enables an operator of instrument 10 to know how far the leading end 17 of tubular section 12 extends out of the distal end of delivery tube 14. This in turn, would enable the depth of a cavity, such as a tooth root canal, or even the rough size of a tumor 63 (see the following discussion on instrument 60) to be measured. The fiber bundle 18 extends out of the rear of handle 32 and is connected to a fiber optic display system (not shown), or in the case of laser cutting, cauterizing and drilling applications, to a source of high energy laser light.

Preferably, one or the other or each of the inside surface of the delivery tube bore 15, the outside surface of the tubular section 12, and for the FIG. 2B embodiment, the bore 24 and the outside surface of the tubular section 22 have an anti-friction coating or are otherwise made to allow each to freely slide past the other. Superelastic or pseudoelastic materials are those that exhibit reversable stress induced martensite when at temperatures above their austenitic finish temperature (Af). Because they can exhibit sufficiently high degrees of stiffness and strength, superelastic materials of particular interest for the present invention are metal alloys such as various well known copper (Cu) alloys and nickel-titanium (Ni—Ti) alloys, including Nitinol and nickel-titanium-niobium (Ni—Ti—Nb) alloys. Some of these materials are capable of being strained up to about 10% or more elastically while still maintaining suitable stiffness. Some of these materials, in particular the copper alloys, exhibit elastic strain limits of up to 16% or more. The superelastic characteristics of such materials are well documented. For example, see the following published works: a book entitled *Engineering Aspects of Shape Memory Alloys*, 1990, published by Butterworth & Heinemann and edited by T. W. Duerig, K. N. Melton, D. Stockel and C. M. Wayman (ISBM No. 0-750-61009-3), including articles therein entitled "An Engineers Perspective of Pseudoelasticity", by T. W. Duerig and R. Zadno, pages 309–393; "An Introduction to Martensite and Shape Memory" by C. M. Wayman and T. W. Duerig, pages 3–20; and "The Mechanical Aspects of Constrained Recovery", by J. L. Proft and T. W. Duerig, pages 115–129, each of which are incorporated by reference herein in their entirety.

Figure 5:
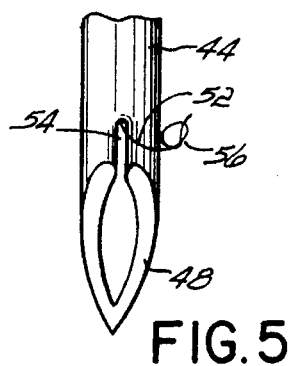
FIG. 5 is an enlarged view of the piercing end of the tubular needle section of FIG. 4.
Figure 4:
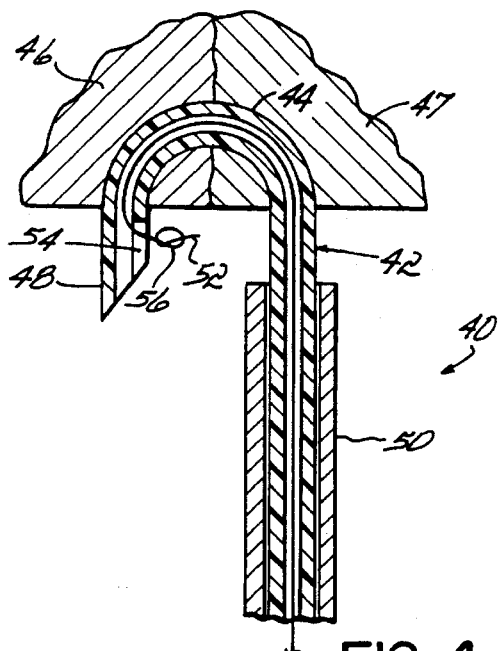
FIG. 4 is a sectional side view of a medical instrument for suturing according to the present invention, with its tubular needle section deployed from the delivery tube.
Figure 6:
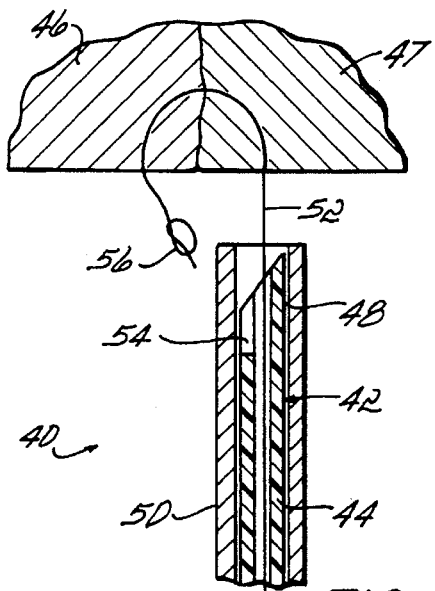
FIG. 6 is a sectional side view of the suturing instrument of FIG. 4, with its tubular needle section fully retracted.

Referring to FIGS. 4–6, another embodiment of the present invention is a medical instrument 40 including a tubular section 42 having a leading end 44 with the shape of a surgical needle, when unconstrained, which is suitable for suturing together pieces 46 and 47 of bodily tissue inside a patient's body. The leading end 44 of the tubular section 42 can have the conventional C-shape of a surgical needle or any other bent or curved shape that facilitates suturing, with its tip 48 being in the form of a sharp point. Because of its superelastic characteristics, this surgical needle 44 can remain straight as it is inserted through a delivery tube 50 without developing a permanent set (i.e., without substantial permanent deformation). While in the delivery tube 50 and in this substantially straight condition, the needle 44 can be delivered to the suturing site through narrower paths then heretofore possible, thereby limiting trauma along the path of insertion. Once at the suture site, the surgical needle 44 is extended out of the leading end of the delivery tube 50, returning it to its original curved or bent shape for suturing. Because the shape of the tubular needle 44 section is variable, suturing can be performed at a variety of angles and orientations relative to the delivery tube 50. Such maneuverability may also be enhanced by using an intermediate tubular section, such as section 22. A suture thread or wire 52 is operatively disposed in the bore of the tubular section 42 with one end extending out the tip 48 through a slot 54 so as to remain in position to form a suture upon removal of the tubular needle from tissue 46,47 (see FIG. 6). It may be necessary to form a knot 56 at the end of thread 52 to insure that the end of thread 52 does not slip through slot 54 and into tubular section 42. As will be described in greater detail later on, a tweezers instrument 90 could be used to grip and tie thread 52 into a suture.

Referring to FIGS. 7 and 8, another embodiment of the present invention is a medical instrument 60 including tubular section 62 adapted to curl around a cancerous tumor or similar mass 63 in a patient's body, such as a woman's breast 64 upon exiting its delivery tube 66. Because such masses 63 are typically denser than the surrounding fatty tissue 65, the locator tube 62 tends to encircle rather than pass through the mass 63. Being surrounded by the locator tube 62, the mass 63 is easier to locate using external imaging systems, like conventional x-rays. However, in order to improve the likelihood of locating the tumor or similar mass 63, the bore of the tubular section 62 is used to inject a radiopaque or other suitable type of dye through its leading end 68 and into the area around the mass 63 to facilitate locating the mass 63 using an external imaging system, such as an X-Ray machine (not shown). Such an instrument 60 could be useful as part of a multi-purpose instrument such as instrument 70 in performing an operation.

Referring to FIG. 9, a multi-purpose instrument 70 according to the present invention can be formed by securing two or more delivery tubes 14, 50 and 72 together in a juxtaposed lengthwise relationship by any suitable means, such as a polymeric jacket 74. Each delivery tube houses a different tool. By being joined together in this manner, the multiple delivery tubes 14, 50 and 72 can be inserted through a single incision, cavity, hollow organ, or other pathway through a patient's body or an object rather than through two or more such pathways. The delivery tubes 14 and 50 respectively house a fiber optic and suture tool as previously described. Delivery tube 72 houses a knife blade 76 having a cutting edge 77. The knife blade 76 is mounted to the leading end 78 of a tubular section 80 by any suitable method. For example, referring to FIG. 10A, the knife blade 76 has a tang 82 fixed in the bore of leading end 78 with a variable locking ring 84 seated in a circumferential groove 85 formed in the outside surface of leading end 78. Variable locking ring 84 is made of a shape memory material, such as nitinol, with a transformation temperature range (TTR). Groove 85 and ring 84 are in an overlapping relation around tang 82. Ring 84 has been trained according to well known shape memory techniques to have an inside diameter at temperatures above its TTR that is smaller than the diameter of groove 85, when unconstrained. Ring 84 has also been trained to have an inside diameter at temperatures below it's TTR that is large enough to allow removal from around groove 85. Ring 84 is sufficiently trained and has suitable mechanical properties to exert a sufficiently strong biasing compressive force at temperatures above it's TTR to lock tang 82 in the bore of leading end 78. A plurality of circumferentially spaced longitudinal slots 88 are preferably formed through the wall of the tubular section 80 at its leading end 78 to facilitate the gripping of tang 82. Instead of using ring 84 and groove 85, the wall of leading end 78 could be made of the shape memory material and trained in the same manner to grip tang 82.

Figure 10B:
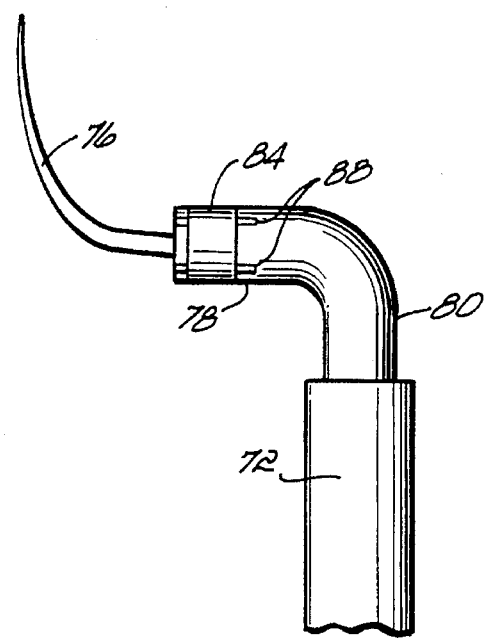
FIG. 10B is a side view of the knife blade component of the instrument of FIG. 9 taken perpendicular to lines 10A—10A, with its knife blade and part of its tubular section extending out of its delivery tube.
Figure 10C:
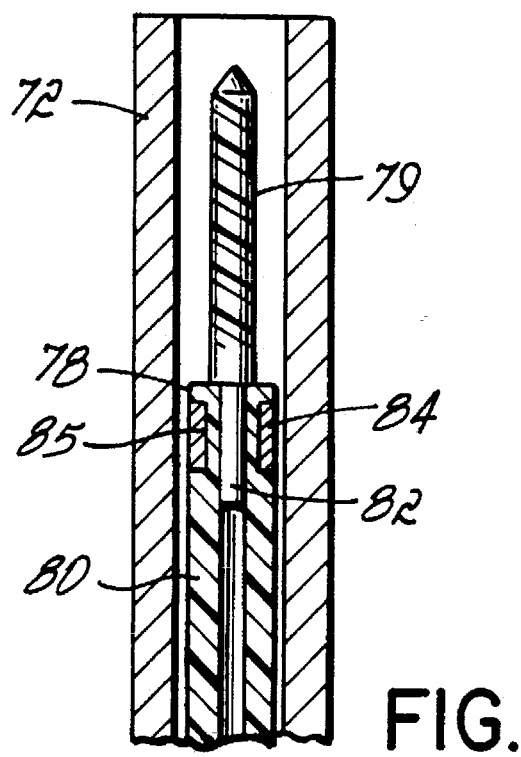
FIG. 10C is a side view similar to FIG. 10A showing a drill bit retracted within the delivery tube.

Referring to FIG. 10B, like previous tubular sections described herein, the leading end 78 of tubular section 80 bends or curves as it extends out of the distal end of delivery tube 72. In addition to tubular section 80, knife blade 76 is also made of a superelastic material. Knife blade 76 can thus have a bent or curved shape suitable for performing a desired procedure when outside of delivery tube 72 and have a substantially straightened shape when retracted back into delivery tube 72, without any resulting permanent deformation. It may be desirable for knife blade 76 to remain substantially straight even outside of tube 72. In such situations, blade 76 could be made of something other than a superelastic material. For example, a hardenable stainless steel may be desirable in order to form a knife blade 76 having a more long lasting cutting edge 77. The edge of blade 76, or any tool used according to the principals of the present invention, could also be hardened with some type of conventional coating or treatment (e.g., diamond, carbide, nitride, etc.). The blade 76 and edge 77 could be adapted for other purposes besides cutting (e.g., scraping, debriding, dissecting, reaming, etc.). It may also be desirable, in some situations, for tubular section 80 to be a simple capillary tube and not made of a superelastic material, as previously discussed above. In addition to some form of blade 76, a variety of alternative tools, such as a pair of tweezers and an ultrasonic vibrating tool with each having its own tang-like structure, could similarly or otherwise be mounted to the leading end 78 of tubular section 80. With the ultrasonic vibrating tool, vibrations are transmitted to the tool through the tubular section 80.

While the multi-purpose instrument 70 is shown with separate delivery tubes 14, 50 and 72 connected together, instrument 70 could also be formed from a single member with two or more bores formed longitudinally therethrough, with each bore housing one of the tools (i.e., fiber optics, surgical needle, locator tube, blade, scissors, forceps, drill bit, tweezers, ultrasonic vibrating tool, etc., to name a few). In addition, two fiber optic instruments, one for viewing and one for directing a laser beam, could be combined into one delivery tube by joining their respective tubular sections together or using a single tubular section with double barrel bores. With such an instrument, a third tool, such as a knife blade, could be mounted to the tubular section(s) between the two fiber optic elements. Similarly, two fiber optic lenses could be mounted on the leading end of the tubular section to provide binocular viewing. The tubular section could also be constructed to fork into two leading ends with one lens mounted on each end and each leading end shaped to bend or curve in opposite directions, for example to view down two branching arteries or other pathways.

Figure 11A:
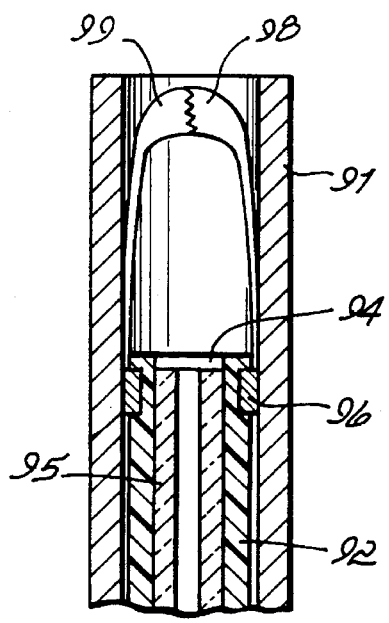
FIG. 11A is a sectional side view of an instrument incorporating fiber optics according to the present invention having a tweezers element, with its fiber optic tubular section and tweezers fully retracted in the delivery tube.
Figure 11B:
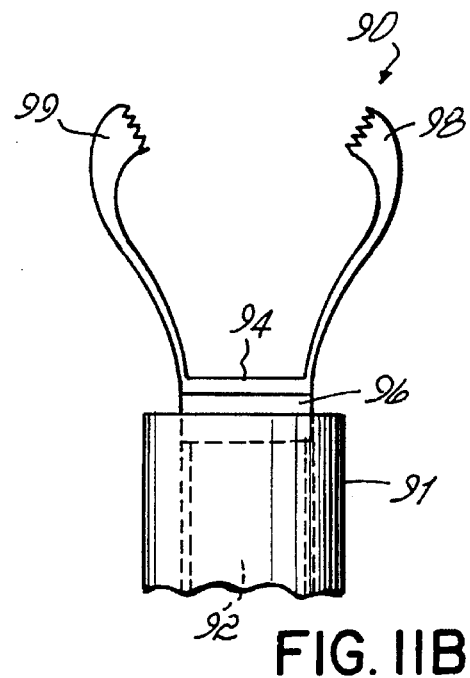
FIG. 11B is a sectional side view of the instrument of FIG. 11A, with its tubular section partially extended and the tweezers element extended out of the delivery tube and in an open condition.

Referring to FIGS. 11A and 11B, rather than using multiple delivery tubes with one tube for each tool, a multipurpose instrument 90 according to the present invention, could combine two or more tools together for simultaneous disposition through a single delivery tube 91. For example, referring to FIGS. 11A and 11B, multi-purpose instrument 90 combines tweezers for gripping an object and fiber optics for viewing the procedure. Such an instrument could be useful as part of a multi-purpose instrument such as instrument 70 in performing a suturing operation or on its own for capturing something. Instrument 90 includes a tubular section 92 having a leading end mounting a fiber optic lens 94 operatively connected to a bundle of optical fibers 95, similar to bundle 18, running through the length of the tubular section 92. The leading end of tubular section 92 includes a circumferential groove, similar to groove 85, formed around its outer surface in which is received a variable locking ring 96 similar to ring 84 in that it is made of a shape memory material having a TTR. Ring 96 is trained to have an inside diameter at temperatures below its TTR that is large enough to allow its removal from the leading end of tubular section 92. Likewise, ring 96 has an inside diameter at temperatures above its TTR that is small enough to prevent its removal from the leading end of tubular section 92. It may also be desirable to use ring 96 to permit the mounting and removal of the lens 94 from the leading end of tubular section 92 at temperatures below its TTR, and to lock the lens 94 in place in the bore at the leading end of tubular section 92 at temperatures above its TTR in the same manner that tang 82 is unlocked from and locked in tubular section 80 by ring 84. Alternatively, the leading end of tubular section 92 could be made of the shape memory material and trained to variably lock lens 94 in place.

Ring 96 mounts a pair of tweezer arms 98 and 99 by any suitable means. In one embodiment, tweezer arm 98 and 99 are closed in a gripping relation when disposed within the delivery tube 91 (see FIG. 11A) and open in a spread apart relation when extended out of delivery tube 91 (see FIG. 11B). One or both of arms 98 and 99 could be made of a superelastic material or any other suitable material, and arms 98 and 99 could have any conventional configuration. Instrument 90 could be provided additional maneuverability in the same manner as shown in FIG. 2B, by inserting tubular section 92 through the bore 24 of the intermediate tubular section 22. In addition, the fiber optics of instrument 90 could be adapted to direct a high-power laser beam for cauterizing, cutting and drilling. Other tools could also be mounted to ring 96 in place of tweezer arms 98 and 99. For example, a knife blade or other blade could be mounted to ring 96.

A hollow tubular section, similar to that shown in FIG. 7, could be provided with a sufficiently sized bore for allowing bodily material to be sucked therethrough. This could be accomplished by having the tubular section in fluid transfer communication with a vacuum source (not shown). The ability to maneuver the tip of the tubular section according to the principles of the present invention disclosed herein could facilitate the suctioning operation. Such an instrument could be useful as part of a multi-purpose instrument such as instrument 70 in performing an operation.

A fiber-optic instrument according to the present invention could be used to aid in various operating procedures, including removing unwanted bodily materials from the patient, to aid in diagnostic procedures, or for any reason. Other tools could also be inserted through the delivery tube for performing a number of additional procedures, for example, a fiber optic laser or a knife blade for cutting tissue, a scraping tool for removing calculus from a tooth, or a vibrating wire for ultrasonic treatments (e.g., pulverizing kidney stones).

From the above disclosure of the general principles of the present invention and the preceding detailed description, those skilled in the art will readily comprehend the various modifications to which the present invention is susceptible. Therefore, the scope of the invention should be limited only by the following claims and equivalents thereof.

What is claimed is:

1. A medical/dental instrument for performing at least one procedure inside a patient's body comprising:

a first tubular section having a bore formed by a wall made of a material exhibiting superelastic characteristics and having a leading end for mounting a tool;

a first delivery tube having a wall forming a bore for receiving said first tubular section therethrough; and an actuating mechanism for moving said first tubular section in and out of and through the bore of said first delivery tube, said first tubular section being substantially straight when its wall is within the bore of said first delivery tube and said first tubular section having a bent or curved shape for performing at least one procedure inside of a patient's body when its wall is disposed outside of said first delivery tube, said leading end of said tubular section including a variable locking element made of a shape memory material having a transformation temperature range, said element permitting the mounting and removal of a tool from said leading end at temperatures below said range, and to lock said tool in place when mounted on said leading end at temperatures above said range, said variable locking element being a ring having an inside diameter, and said leading end of said tubular section having an outside diameter for receiving said ring, said inside diameter being larger than said outside diameter at temperatures below said range, and when unconstrained, said inside diameter being smaller than said outside diameter at temperatures above said range.

2. The instrument claim 1, said delivery tube having a leading end and said tubular section having a substantially straight longitudinal axis when disposed within the bore of said delivery tube, said tubular section being bent or curved at an angle from said longitudinal axis when disposed outside of said delivery tube, said angle being variable by varying the extent said tubular section is disposed outside of the leading end of said delivery tube, and said tubular section being sufficiently stiff to permit the leading end of said tubular section to be rotated around said longitudinal axis.

3. The instrument of claim 1, said tubular section having a coiled shape when operatively disposed outside of said delivery tube.

4. The instrument of claim 1, said tubular section having an optical fiber disposed therethrough and a leading end, said optical fiber for transmitting high-power laser beams from said leading end.

5. The instrument of claim 1, said tubular section having a leading end with a sharp point and a suitable needle shape for suturing inside of a patient's body when disposed outside of said delivery tube.

6. The instrument of claim 5, a suture thread or wire being operatively disposed in the bore of said tubular section.

7. The instrument of claim 1, said tubular section being operatively adapted to curl around a tumor or similar mass upon exiting said delivery tube, and the bore of said tubular section being in fluid transfer communication with a source of dye detectable by an external imaging system when disposed in a patient's body.

8. The instrument of claim 1, the bore of said tubular section being of a size suitable for having bodily material suctioned therethrough and being in fluid transfer communication with a vacuum source.

9. The instrument of claim 1 including a plurality of tubular sections and corresponding delivery tubes, said delivery tubes being fixed in a longitudinally juxtaposed position alongside one another, and each of said tubular sections having said bent or curved shape when disposed outside of its corresponding delivery tube.

10. The instrument of claim 1, including a second delivery tube fixed in a longitudinally juxtaposed position alongside said first delivery tube, said tubular section having an optical fiber disposed therethrough and a leading end, said optical fiber being operatively adapted for transmitting an image from said leading end through said tubular section to view inside a patient's body.

11. The instrument of claim 10, said second delivery tube having a bore adapted to slidably receive a tool therethrough.

12. The instrument of claim 11, said tool being one of a group of tools consisting of a blade, tweezers, a drill bit, a needle, forceps, scissors and an ultrasonic vibrating tool.

13. The instrument of claim 1, said tool being a knife blade having at least one free edge operatively adapted for at least one of a group of purposes consisting of debriding, dissecting, scraping reaming, and cutting when extended from its delivery tube.

14. The instrument of claim 1, said tool being a knife blade made of a material exhibiting superelastic characteristics, said knife blade having a longitudinal axis that is substantially straight when said blade is disposed within the bore of said delivery tube and bent or curved when said blade is disposed outside of said delivery tube.

15. The instrument of claim 1, said tool being one of a group of tools consisting of a blade, tweezers, a drill bit, a needle, forceps, scissors and an ultrasonic vibrating tool.

16. The instrument of claim 1, said tool being one of a group of tools consisting of a blade, tweezers, a drill bit, a needle, forceps, scissors and an ultrasonic vibrating tool, and the leading end of said tubular section also mounting at least one fiber optic lens in optical communication with an optical fiber disposed through the bore of said tubular section.

17. The instrument of claim 1 including a bendable shaft mounting a tool, the bore of said tubular section being adapted to slidably receive said shaft mounted tool therethrough.

18. The instrument of claim 17, said tool being a drill bit.

19. The instrument of claim 1 further including a part in the distal section of the instrument that can be bent into a stable, non-straight configuration.

20. The instrument of claim 19 wherein said bendable part is made from a shape memory alloy having a transformation temperature to austenite above ambient body temperature.

21. The instrument of claim 20 wherein said bendable part is at least a part of the delivery tube.

22. The instrument of claim 20 wherein said bendable part is at least a part of the first tubular section.

23. The instrument of claim 20 wherein said bendable part is a shaft placed parallel to at least a section of the length axis of the instrument.

24. A medical/dental instrument for performing at least one procedure inside a patient's body comprising:

a first tubular section having a bore formed by a wall made of a material exhibiting superelastic characteristics;

a first delivery tube having a wall forming a bore for receiving said first tubular section therethrough;

an actuating mechanism for moving said first tubular section in and out of and through the bore of said first delivery tube, said first tubular section being substantially straight when its wall is within the bore of said first delivery tube and said first tubular section having a bent or curved shape for performing at least one procedure inside of a patient's body when its wall is disposed outside of said first delivery tube; and a second tubular section having a bore formed by a wall made of a material exhibiting superelastic characteristics, said second tubular section being concentrically disposed within said first tubular section, being substantially straight when its wall is within the bore of said first tubular section and having a bend or curved shape when its wall is disposed outside of said first tubular section, and said actuating mechanism being able to move said second tubular section in and out of and through the bore of said first tubular section independent of the movement of said first tubular section in and out of and through said delivery tube, said second tubular section including a leading end and a variable locking element made of a shape memory material having a transformation temperature range, said locking element permitting the mounting and removal of a tool from said leading end at temperatures below said range, and locking said tool in place when mounted on said leading end at temperatures above said range, said variable locking element being a ring having an inside diameter, and said leading end of said second tubular section having an outside diameter for receiving said ring, said inside diameter being larger than said outside diameter at temperatures below said range, and when unconstrained, said inside diameter being smaller than said outside diameter at temperatures above said range.

25. An instrument for transmitting images through an optical fiber comprising:

a first tubular section having a leading end and a wall made of a material exhibiting superelastic characteristics which forms a bore with an optical fiber disposed therethrough, said optical fiber for transmitting an image from said leading end through said first tubular section, said leading end of said tubular section mounting at least one fiber optic lens in optical communication with said optical fiber, said leading end including a variable locking element made of a shape memory material having a transformation temperature range, said element permitting the mounting and removal of said at least one lens from said leading end at temperatures below said range, and to lock said at least one lens in place when mounted on said leading end at temperatures above said range, said variable locking element being a ring having an inside diameter, and the leading end of said tubular section having an outside diameter for receiving said ring, said inside diameter being larger than said outside diameter at temperatures below said range, and when unconstrained, said inside diameter being smaller than said outside diameter at temperatures above said range;

a first delivery tube having a wall forming a bore for receiving said first tubular section therethrough; and an actuating mechanism for moving said first tubular section in and out of and through the bore of said first delivery tube, said first tubular section being substantially straight when its wall is within the bore of said first delivery tube and said first tubular section having a bend or curved shape when its wall is disposed outside of said first delivery tube.

26. The instrument of claim 25 further including a part in the distal section of the instrument that can be bent into a stable, non-straight configuration.

27. The instrument of claim 26 wherein said bendable part is made from a shape memory alloy having a transformation temperature to austenite above ambient body temperature.

28. The instrument of claim 27 wherein said bendable part is at least a part of the delivery tube.

29. The instrument of claim 27 wherein said bendable part is at least a part of the first tubular section.

30. The instrument of claim 27 wherein said bendable part is a shaft placed parallel to at least a section of the length axis of the instrument.

* * * * *